(12) United States Patent
Bateman et al.

(10) Patent No.: US 10,319,577 B2
(45) Date of Patent: Jun. 11, 2019

(54) COMBINED MASS-TO-CHARGE RATIO AND CHARGE STATE SELECTION IN TANDEM MASS SPECTROMETRY

(71) Applicant: Micromass UK Limited, Wilmslow (GB)

(72) Inventors: Robert Harold Bateman, Knutsford (GB); Kevin Giles, Stockport (GB); Steven Derek Pringle, Darwen (GB); Jason Lee Wildgoose, Stockport (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/626,447

(22) Filed: Jun. 19, 2017

(65) Prior Publication Data

US 2017/0287692 A1  Oct. 5, 2017

Related U.S. Application Data

(63) Continuation of application No. 12/514,972, filed as application No. PCT/GB2007/004364 on Nov. 15, 2007, now Pat. No. 9,685,313.

(60) Provisional application No. 60/869,366, filed on Dec. 11, 2006.

(30) Foreign Application Priority Data

Nov. 15, 2006 (GB) .................................. 0622780.5

(51) Int. Cl.
*H01J 49/00* (2006.01)
*H01J 49/42* (2006.01)
*G01N 27/62* (2006.01)

(52) U.S. Cl.
CPC ........ *H01J 49/4215* (2013.01); *G01N 27/622* (2013.01); *H01J 49/004* (2013.01); *H01J 49/426* (2013.01)

(58) Field of Classification Search
CPC ...... H01J 49/00; H01J 49/0031; H01J 49/004; H01J 49/0045; H01J 49/005; H01J 49/02; H01J 49/06; H01J 49/061; H01J 49/062; H01J 49/063; H01J 49/065
USPC .......................... 250/281, 282, 283, 286, 287
See application file for complete search history.

(56) References Cited

U.S. PATENT DOCUMENTS

| 4,221,964 | A | 9/1980 | Schlereth et al. |
| 4,234,791 | A | 11/1980 | Enke et al. |
| 5,572,035 | A | 11/1996 | Franzen |
| 6,177,668 | B1 | 1/2001 | Hager |
| 6,504,148 | B1 | 1/2003 | Hager |
| 6,753,523 | B1 | 6/2004 | Whitehouse et al. |
| 6,828,551 | B2 | 12/2004 | Kato |
| 6,906,319 | B2 | 6/2005 | Hoyes |

(Continued)

FOREIGN PATENT DOCUMENTS

| GB | 2382919 | 6/2003 |
| GB | 2389704 | 12/2003 |

(Continued)

*Primary Examiner* — Jason L McCormack

(57) ABSTRACT

A mass spectrometer is disclosed comprising an ion mobility spectrometer and an ion gate. A collision cell is arranged downstream of the ion gate. The operation of the ion mobility spectrometer and the ion gate are synchronized so that only ions having a particular mass to charge ration and a desired charge state are onwardly transmitted to the collision cell.

16 Claims, 6 Drawing Sheets

(56) References Cited

U.S. PATENT DOCUMENTS

| | | | |
|---|---|---|---|
| 6,940,065 B2 | 9/2005 | Graber et al. | |
| 6,953,928 B2 | 10/2005 | Vestal et al. | |
| 7,161,146 B2 | 1/2007 | Doroshenko et al. | |
| 9,685,313 B2* | 6/2017 | Bateman | G01N 27/622 |
| 2002/0014586 A1* | 2/2002 | Clemmer | G01N 27/622 |
| | | | 250/287 |
| 2002/0175279 A1 | 11/2002 | Hager | |
| 2003/0001084 A1* | 1/2003 | Bateman | H01J 49/004 |
| | | | 250/281 |
| 2003/0038235 A1 | 2/2003 | Guevremont et al. | |
| 2004/0094702 A1 | 5/2004 | Clemmer | |
| 2004/0245452 A1* | 12/2004 | Bateman | G01N 27/622 |
| | | | 250/287 |
| 2005/0051719 A1 | 3/2005 | Miller et al. | |
| 2005/0092911 A1 | 5/2005 | Hoyes | |
| 2005/0242281 A1 | 11/2005 | Li | |
| 2005/0253059 A1 | 11/2005 | Goeringer et al. | |
| 2007/0114382 A1 | 5/2007 | Clemmer et al. | |

FOREIGN PATENT DOCUMENTS

| | | |
|---|---|---|
| GB | 2421842 | 7/2006 |
| GB | 2437829 | 11/2007 |
| WO | 2005/098899 | 10/2005 |
| WO | 2006/054101 | 5/2006 |
| WO | 2006/061593 | 6/2006 |

\* cited by examiner

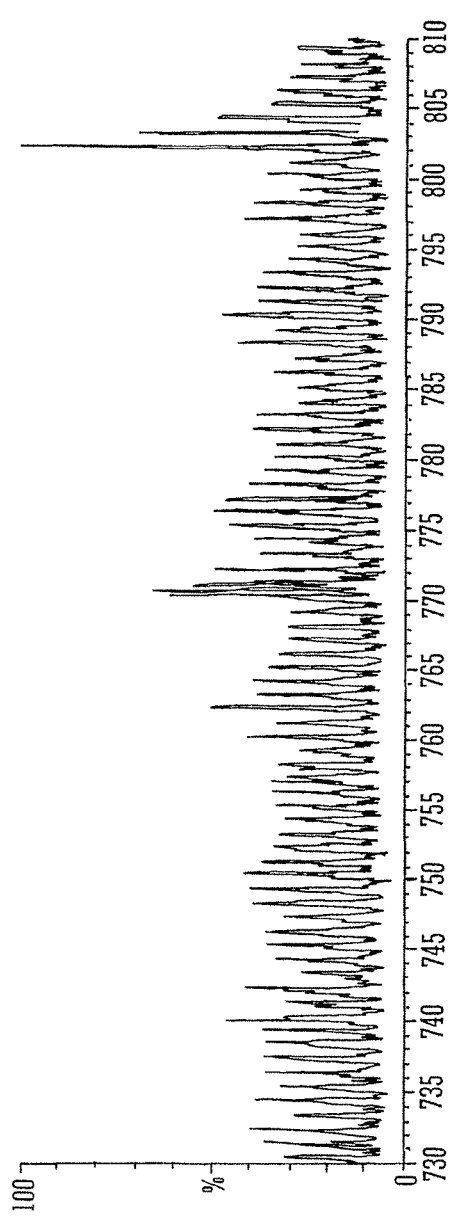
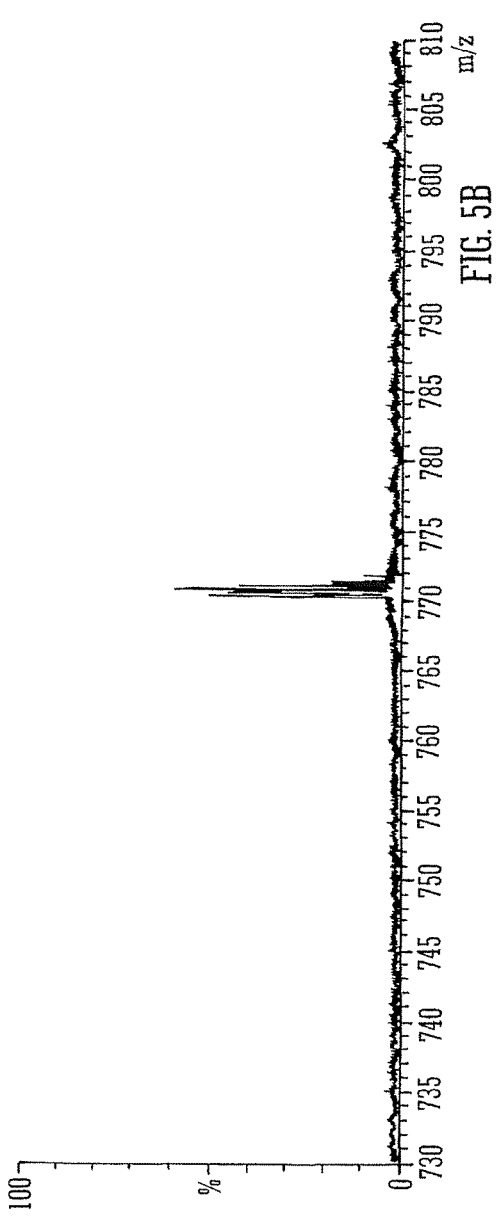

COMBINED MASS-TO-CHARGE RATIO AND CHARGE STATE SELECTION IN TANDEM MASS SPECTROMETRY

CROSS REFERENCE TO RELATED APPLICATIONS

This application is a continuation of U.S. application Ser. No. 12/514,972, which is the National Stage of International Application No. PCT/GB07/004364, filed Nov. 15, 2007, which claims priority to and benefit of U.S. Provisional Patent Application Ser. No. 60/869,366, filed Dec. 11, 2006, and priority to and benefit of United Kingdom Patent Application No. 0622780.5, filed Nov. 15, 2006. The entire contents of these applications are incorporated herein by reference.

BACKGROUND OF THE INVENTION

The present invention relates to a mass spectrometer and a method of mass spectrometry.

Tandem mass spectrometry or MS/MS has become the preferred technology for many applications in which mass spectrometry plays a part. Firstly, tandem mass spectrometry allows selection and isolation of specific compounds of interest and their subsequent identification. Secondly, the extra selectivity of MS/MS enables this technology to be used for quantification of target compounds even in the presence of complex matrices.

A known tandem mass spectrometer comprises two mass filters or analysers arranged in series with a collision cell arranged in between the two mass filters or analysers. Ions selected by the first mass filter are arranged to undergo collision-induced decomposition (CID) in the collision cell wherein ions undergo collisions with gas molecules. The second mass analyser is arranged to analyse the products of the fragmentation process. The processes of mass selection, fragmentation and product ion mass analysis take place sequentially in space.

The most common form of tandem mass spectrometer is generally known as a triple quadrupole mass spectrometer. A triple quadrupole tandem mass spectrometer comprises a first quadrupole mass filter (MS1) followed by a gas collision cell. The gas collision cell is followed by a second quadrupole mass filter (MS2). The name triple quadrupole is derived from the first such instrument in which a RF quadrupole rod set ion guide was used as the gas collision cell. The quadrupole mass filters are typically used to transmit ions having a specific mass to charge ratio. Therefore, in order to record a full mass spectrum, the quadrupole mass filters must be scanned across the full mass to charge ratio spectrum in order to transmit ions sequentially having different mass to charge ratios. The duty cycle for this process is therefore relatively low and as a consequence the sensitivity of the quadrupole mass filter used to record a full spectrum is relatively poor. On the other hand, the quadrupole mass filter will have 100% duty cycle when used to transmit ions having a specific mass to charge ratio.

A triple quadrupole mass spectrometer may be used in a Selected Reaction Monitoring ("SRM") mode of operation wherein ions having a single mass to charge ratio are transmitted through the first mass filter (MS1) and the second mass filter (MS2) is set to monitor for fragment or daughter ions having a specific mass to charge ratio. Such an arrangement is very specific and exceptionally sensitive. Triple quadrupole mass spectrometers have, as a result, found significant use in drug discovery and development processes where they may be used either in a Selected Reaction Monitoring mode of operation or in either a related Multiple Reaction Monitoring ("MRM") mode of operation to quantify target compounds of biological significance.

More recently, triple quadrupole mass spectrometers have been used in the study of protein biomarkers. For example, a protein extract may be analysed to determine which proteins may be used as biomarkers in order to indicate the occurrence of a specific medical disorder or to measure the response to specific medication. Such biomarkers may subsequently be monitored as an aid to medical diagnosis and/or as a means of monitoring therapeutic response. A sample may first be extracted from biological fluids or tissue e.g. blood plasma or serum, urine, saliva, body tissue etc. Proteins, or a sub-group of proteins, may then be extracted from the biological fluid or tissue using one or more known extraction methods e.g. methods based on protein size, polarity, solubility, hydrophobicity, chemical affinity, molecular affinity etc. The resulting protein mixture may then be digested (for example using the digestion enzyme trypsin) and the resulting mixture of peptides is then submitted for separation by chromatography and analysis by mass spectrometry.

The peptide mixture may typically be separated by liquid chromatography. The individual components eluting from the chromatography column may be ionised by, for example, Electrospray ionisation. Specific targeted peptides may be detected by mass spectrometry e.g. by using a triple quadrupole mass spectrometer operating in a Selected Reaction Monitoring (SRM) mode of operation. As already discussed, such an arrangement provides a very specific and a very sensitive method of analysis which is also capable of accurately quantifying the amount of the targeted peptides present. This in turn may be used to quantify the amount of specific targeted proteins present in the original sample.

Despite the high specificity and the high sensitivity of the known method, detection limits and quantification limits are still often imposed by chemical background present in the protein digest. The peptides eluting from the chromatography column and subsequently ionised by Electrospray ionisation will commonly give rise to doubly or triply charged ions but other material eluting from the chromatography column at the same time will commonly yield a low background level of singly charged ions throughout the mass spectrum. As a consequence, singly charged chemical matrix background ions having similar mass to charge ratios as the targeted peptides will also appear in the resulting mass spectrum. This can, in some situations, impose a limitation on the detection and quantification of some of the targeted peptides. In some instances, where the protein relative abundance is very low, the peptide ions of interest may be totally obscured by background chemical matrix ions.

It is therefore desired to provide an improved mass spectrometer and method of mass spectrometry.

SUMMARY OF THE INVENTION

According to an aspect of the present invention there is provided a mass spectrometer comprising:
a first mass to charge ratio filter or mass to charge ratio mass analyser arranged and adapted in a first mode of operation to transmit parent or precursor ions having a mass to charge ratio within a first range;
an ion mobility spectrometer or separator;
attenuation means for attenuating or diverting ions in a mode of operation;
a collision, fragmentation or reaction device; and a control device arranged and adapted to control the operation of the attenuation means so that ions having mass to charge ratios within the first range but having one or more undesired first charge states are substantially attenuated.

The first mass to charge ratio filter or mass to charge ratio mass analyser is preferably arranged and adapted in the first mode of operation to attenuate ions having mass to charge ratios outside of the first range. The first range preferably falls within a mass to charge ratio range selected from the group consisting of: (i) <50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; (xxi) 1000-1050; (xii) 1050-1100; (xxiii) 1100-1150; (xxiv) 1150-1200; (xxv) 1200-1250; (xxvi) 1250-1300; (xvii) 1300-1350; (xxviii) 1350-1400; (xxix) 1400-1450; (xxx) 1450-1500; (xxxi) 1500-1550; (xxxii) 1550-1600; (xxxiii) 1600-1650; (xxxiv) 1650-1700; (xxxv) 1700-1750; (xxxvi) 1750-1800; (xxxvii) 1800-1850; (xxxviii) 1850-1900; (xxxix) 1900-1950; (xl) 1950-2000; and (xli) >2000. The first range preferably has a width selected from the group consisting of: (i) <0.5 atomic mass units; (ii) 0.5-1.0 atomic mass units; (iii) 1.0-1.5 atomic mass units; (iv) 1.5-2.0 atomic mass units; (v) 2.0-2.5 atomic mass units; (vi) 2.5-3.0 atomic mass units; (vii) 3.0-3.5 atomic mass units; (viii) 3.5-4.0 atomic mass units; (ix) 4.0-4.5 atomic mass units; (x) 4.5-5.0 atomic mass units; and (xi) >5.0 atomic mass units.

The attenuation means preferably comprises an ion gate, ion deflector or ion barrier. The ion mobility spectrometer or separator is preferably arranged upstream and/or downstream of the attenuation means.

According to a less preferred embodiment the attenuation means may comprise means for removing, attenuating or reducing the amplitude of an AC or RF voltage or potential which is applied to at least a portion of the ion mobility spectrometer or separator. The attenuation means preferably removes, attenuates or reduces the amplitude of an AC or RF voltage or potential which is applied to at least a portion of the ion mobility spectrometer or separator so that ions within at least a portion of the ion mobility spectrometer or separator are no longer confined radially within the ion mobility spectrometer or separator.

The attenuation means may comprise means for removing, attenuating or reducing the amplitude of an AC or RF voltage or potential which is applied to at least a portion of an ion guide or other ion optical device which is preferably arranged upstream and/or downstream of the ion mobility spectrometer or separator. The attenuation means preferably removes, attenuates or reduces the amplitude of an AC or RF voltage or potential which is applied to at least a portion of the ion guide or other ion optical device which is arranged upstream and/or downstream of the ion mobility spectrometer or separator so that ions within at least a portion of the ion guide or other ion optical device are no longer confined radially within the ion guide or other ion optical device.

The attenuation means is preferably arranged to transmit ions during a first time period or first time window. The attenuation means is preferably arranged to attenuate and/or divert ions during a second time period or second time window, wherein the second time period or second time window is different from the first time period or first time window. The attenuation means is preferably also arranged to attenuate and/or divert ions during a third time period or third time window, wherein the third time period or third time window is different from the second time period or second time window and wherein the third time period or third time window is also different from the first time period or first time window. According to an embodiment, the second time period or second time window is intermediate the first time period or first time window and the third time period or third time window.

According to the preferred embodiment the first undesired charge state is preferably selected from one or more of the following: (i) singly charged; (ii) doubly charged; (iii) triply charged; (iv) quadruply charged; (v) quintuply; and (vi) multiply charged. According to an embodiment singly charged ions are attenuated or diverted by the attenuation means whereas doubly charged or multiply charges ions are onwardly transmitted by the attenuation means to the collision, fragmentation or reaction device.

The ion mobility spectrometer or separator preferably comprises a gas phase electrophoresis device.

According to an embodiment the ion mobility spectrometer or separator may comprise:
(i) a drift tube;
(ii) a multipole rod set or a segmented multipole rod set;
(iii) an ion tunnel or ion funnel; or
(iv) a stack or array of planar, plate or mesh electrodes.

The drift tube preferably comprises one or more electrodes and means for maintaining an axial DC voltage gradient or a substantially constant or linear axial DC voltage gradient along at least 5%, 10%, 15%, 20%, 25%, 30%, 35%, 40%, 45%, 50%, 55%, 60%, 65%, 70%, 75%, 80%, 85%, 90%, 95% or 100% of the axial length of the drift tube.

The multipole rod set preferably comprises a quadrupole rod set, a hexapole rod set, an octapole rod set or a rod set comprising more than eight rods.

The ion tunnel or ion funnel preferably comprises a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area.

At least 5%, 10%, 15%, 20%, 25%, 30%, 35%, 40%, 45%, 50%, 55%, 60%, 65%, 70%, 75%, 80%, 85%, 90%, 95% or 100% of the electrodes preferably have internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) >10.0 mm.

The stack or array of planar, plate or mesh electrodes preferably comprises a plurality or at least 2, 3, 4, 5, 6, 7, 8, 9, 10, 11, 12, 13, 14, 15, 16, 17, 18, 19 or 20 planar, plate or mesh electrodes wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use. At least some or at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are preferably supplied with an AC or RF voltage and wherein adjacent planar, plate or mesh electrodes are preferably supplied with opposite phases of the AC or RF voltage.

The ion mobility spectrometer or separator preferably comprises a plurality of axial segments or at least 5, 10, 15, 20, 25, 30, 35, 40, 45, 50, 55, 60, 65, 70, 75, 80, 85, 90, 95 or 100 axial segments.

The mass spectrometer preferably further comprises DC voltage means for maintaining a substantially constant DC voltage gradient along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator in order to urge at least some ions along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

The mass spectrometer preferably further comprises transient DC voltage means arranged and adapted to apply one or more transient DC voltages or potentials or one or more transient DC voltage or potential waveforms to at least some of the electrodes forming the ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

The mass spectrometer preferably further comprises AC or RF voltage means arranged and adapted to apply two or more phase-shifted AC or RF voltages to electrodes forming the ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

The ion mobility spectrometer or separator preferably has an axial length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

The ion mobility spectrometer or separator preferably further comprises AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the electrodes forming the ion mobility spectrometer or separator in order to confine ions radially within the ion mobility spectrometer or separator. The AC or RF voltage means is preferably arranged and adapted to supply an AC or RF voltage to the electrodes of the ion mobility spectrometer or separator having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak. The AC or RF voltage means is preferably arranged and adapted to supply an AC or RF voltage to the electrodes of the ion mobility spectrometer or separator having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

According to an embodiment singly charged ions having a mass to charge ratio in the range of 1-100, 100-200, 200-300, 300-400, 400-500, 500-600, 600-700, 700-800, 800-900, 900-1000 or >1000 have a drift or transit time through the ion mobility spectrometer or separator in the range: (i) 0-1 ms; (ii) 1-2 ms; (iii) 2-3 ms; (iv) 3-4 ms; (v) 4-5 ms; (vi) 5-6 ms; (vii) 6-7 ms; (viii) 7-8 ms; (ix) 8-9 ms; (x) 9-10 ms; (xi) 10-11 ms; (xii) 11-12 ms; (xiii) 12-13 ms; (xiv) 13-14 ms; (xv) 14-15 ms; (xvi) 15-16 ms; (xvii) 16-17 ms; (xviii) 17-18 ms; (xix) 18-19 ms; (xx) 19-20 ms; (xxi) 20-21 ms; (xxii) 21-22 ms; (xxiii) 22-23 ms; (xxiv) 23-24 ms; (xxv) 24-25 ms; (xxvi) 25-26 ms; (xxvii) 26-27 ms; (xxviii) 27-28 ms; (xxix) 28-29 ms; (xxx) 29-30 ms; (xxxi) 30-35 ms; (xxxii) 35-40 ms; (xxxiii) 40-45 ms; (xxxiv) 45-50 ms; (xxxv) 50-55 ms; (xxxvi) 55-60 ms; (xxxvii) 60-65 ms; (xxxviii) 65-70 ms; (xxxix) 70-75 ms; (xl) 75-80 ms; (xli) 80-85 ms; (xlii) 85-90 ms; (xliii) 90-95 ms; (xliv) 95-100 ms; and (xlv) >100 ms.

The mass spectrometer preferably further comprises a device arranged and adapted to maintain at least a portion of the ion mobility spectrometer or separator at a pressure selected from the group consisting of: (i) >0.001 mbar; (ii) >0.01 mbar; (iii) >0.1 mbar; (iv) >1 mbar; (v) >10 mbar; (vi) >100 mbar; (vii) 0.001-100 mbar; (viii) 0.01-10 mbar; and (ix) 0.1-1 mbar.

The mass spectrometer preferably further comprises a device arranged and adapted to maintain at least a portion of the ion mobility spectrometer or separator at a pressure selected from the group consisting of: (i) <0.1 mbar; (ii) ≥0.1 mbar; (iii) ≥0.2 mbar; (iv) ≥0.3 mbar; (v) ≥0.4 mbar; (vi) ≥0.5 mbar; (vii) ≥0.6 mbar; (viii) ≥0.7 mbar; (ix) ≥0.8 mbar; (x) ≥0.9 mbar; (xi) ≥1.0 mbar; (xii) ≥1.1 mbar; (xiii) ≥1.2 mbar; (xiv) ≥1.3 mbar; (xv) ≥1.4 mbar; (xvi) ≥1.5 mbar; (xvii) ≥1.6 mbar; (xviii) ≥1.7 mbar; (xix) ≥1.8 mbar; (xx) ≥1.9 mbar; (xxi) ≥2.0 mbar; (xxii) ≥3.0 mbar; (xxiii) ≥4.0 mbar; (xxiv) ≥5.0 mbar; (xxv) ≥6.0 mbar; (xxvi) ≥7.0 mbar; (xxvii) ≥8.0 mbar; (xxviii) ≥9.0 mbar; and (xxix) ≥10.0 mbar.

The mass spectrometer preferably further comprises a device arranged and adapted to maintain at least a portion of the ion mobility spectrometer or separator at a pressure selected from the group consisting of: (i) 0.1-0.5 mbar; (ii) 0.5-1.0 mbar; (iii) 1.0-1.5 mbar; (iv) 1.5-2.0 mbar; (v) 2.0-2.5 mbar; (vi) 2.5-3.0 mbar; (vii) 3.0-3.5 mbar; (viii) 3.5-4.0 mbar; (ix) 4.0-4.5 mbar; (x) 4.5-5.0 mbar; (xi) 5.0-5.5 mbar; (xii) 5.5-6.0 mbar; (xiii) 6.0-6.5 mbar; (xiv) 6.5-7.0 mbar; (xv) 7.0-7.5 mbar; (xvi) 7.5-8.0 mbar; (xvii) 8.0-8.5 mbar; (xviii) 8.5-9.0 mbar; (xix) 9.0-9.5 mbar; and (xx) 9.5-10.0 mbar.

According to the preferred embodiment the collision, fragmentation or reaction device is preferably arranged and adapted to fragment ions by Collision Induced Dissociation ("CID").

According to less preferred embodiments, the collision, fragmentation or reaction device may be selected from the group consisting of: (i) a Surface Induced Dissociation ("SID") fragmentation device; (ii) an Electron Transfer Dissociation fragmentation device; (iii) an Electron Capture Dissociation fragmentation device; (iv) an Electron Collision or Impact Dissociation fragmentation device; (v) a Photo Induced Dissociation ("PID") fragmentation device; (vi) a Laser Induced Dissociation fragmentation device; (vii) an infrared radiation induced dissociation device; (viii) an ultraviolet radiation induced dissociation device; (ix) a nozzle-skimmer interface fragmentation device; (x) an in-source fragmentation device; (xi) an ion-source Collision Induced Dissociation fragmentation device; (xii) a thermal or temperature source fragmentation device; (xiii) an electric field induced fragmentation device; (xiv) a magnetic field induced fragmentation device; (xv) an enzyme digestion or enzyme degradation fragmentation device; (xvi) an ion-ion reaction fragmentation device; (xvii) an ion-molecule reaction fragmentation device; (xviii) an ion-atom reaction fragmentation device; (xix) an ion-metastable ion reaction fragmentation device; (xx) an ion-metastable molecule reaction fragmentation device; (xxi) an ion-metastable atom reaction fragmentation device; (xxii) an ion-ion reaction device for reacting ions to form adduct or product ions; (xxiii) an ion-molecule reaction device for reacting ions to form adduct or product ions; (xxiv) an ion-atom reaction device for reacting ions to form adduct or product ions; (xxv) an ion-metastable ion reaction device for reacting ions to form adduct or product ions; (xxvi) an ion-metastable molecule reaction device for reacting ions to form adduct or product ions; and (xxvii) an ion-metastable atom reaction device for reacting ions to form adduct or product ions.

The collision, fragmentation or reaction device preferably comprises:
(i) a multipole rod set or a segmented multipole rod set;
(ii) an ion tunnel or ion funnel; or
(iii) a stack or array of planar, plate or mesh electrodes.

The multipole rod set preferably comprises a quadrupole rod set, a hexapole rod set, an octapole rod set or a rod set comprising more than eight rods.

The ion tunnel or ion funnel preferably comprises a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area. Preferably, at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) >10.0 mm.

The stack or array of planar, plate or mesh electrodes preferably comprises a plurality or at least 2, 3, 4, 5, 6, 7, 8, 9, 10, 11, 12, 13, 14, 15, 16, 17, 18, 19 or 20 planar, plate or mesh electrodes arranged generally in the plane in which ions travel in use, wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use.

The mass spectrometer preferably further comprises AC or RF voltage means for supplying the plurality of planar, plate or mesh electrodes with an AC or RF voltage and wherein adjacent planar, plate or mesh electrodes are preferably supplied with opposite phases of the AC or RF voltage.

According to an embodiment the collision, fragmentation or reaction device may comprise a plurality of axial segments or at least 5, 10, 15, 20, 25, 30, 35, 40, 45, 50, 55, 60, 65, 70, 75, 80, 85, 90, 95 or 100 axial segments.

The mass spectrometer may further comprise transient DC voltage means arranged and adapted to apply one or more transient DC voltages or potentials or one or more transient DC voltage or potential waveforms to electrodes forming the collision, fragmentation or reaction device in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the collision, fragmentation or reaction device.

The mass spectrometer may further comprise AC or RF voltage means arranged and adapted to apply two or more phase-shifted AC or RF voltages to electrodes forming the collision, fragmentation or reaction device in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the collision, fragmentation or reaction device.

The collision, fragmentation or reaction device preferably has an axial length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

The collision, fragmentation or reaction device preferably further comprises AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the plurality of electrodes of the collision, fragmentation or reaction device in order to confine ions radially within the collision, fragmentation or reaction device. The AC or RF voltage means is preferably arranged and adapted to supply an AC or RF voltage to the plurality of electrodes of the collision, fragmentation or reaction device having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak. The AC or RF voltage means is preferably arranged and adapted to supply an AC or RF voltage to the plurality of electrodes of the collision, fragmentation or reaction device having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

According to the preferred embodiment singly charged ions having a mass to charge ratio in the range of 1-100, 100-200, 200-300, 300-400, 400-500, 500-600, 600-700, 700-800, 800-900 or 900-1000 have a drift or transit time through the collision, fragmentation or reaction device in the range: (i) 0-10 µs; (ii) 10-20 µs; (iii) 20-30 µS; (iv) 30-40 µs; (v) 40-50 µs; (vi) 50-60 µs; (vii) 60-70 µs; (viii) 70-80 µs; (ix) 80-90 µs; (x) 90-100 µs; (xi) 100-110 µs; (xii) 110-120 µs; (xiii) 120-130 µs; (xiv) 130-140 µs; (xv) 140-150 µs; (xvi) 150-160 µs; (xvii) 160-170 µs; (xviii) 170-180 µs; (xix) 180-190 µs; (xx) 190-200 µs; (xxi) 200-210 µs; (xxii) 210-220 µs; (xxiii) 220-230 µs; (xxiv) 230-240 µs; (xxv) 240-250 µs; (xxvi) 250-260 µs; (xxvii) 260-270 µs; (xxviii) 270-280 µs; (xxix) 280-290 µs; (xxx) 290-300 µs; and (xxxi) >300 µs.

The mass spectrometer preferably further comprises means arranged and adapted to maintain at least a portion of the collision, fragmentation or reaction device at a pressure selected from the group consisting of: (i) >0.0001 mbar; (ii)

>0.001 mbar; (iii) >0.01 mbar; (iv) >0.1 mbar; (v) >1 mbar; (vi) >10 mbar; (vii) 0.0001-0.1 mbar; and (viii) 0.001-0.01 mbar.

The mass spectrometer preferably further comprises acceleration means arranged and adapted to accelerate ions into the collision, fragmentation or reaction device wherein in a mode of operation at least 5%, 10%, 15%, 20%, 25%, 30%, 35%, 40%, 45%, 50%, 55%, 60%, 65%, 70%, 75%, 80%, 85%, 90%, 95% or 100% of the ions are caused to fragment or react upon entering the collision, fragmentation or reaction device.

The mass spectrometer preferably further comprises a control system arranged and adapted to switch or repeatedly switch the potential difference through which ions pass prior to entering the collision, fragmentation or reaction device between a relatively high fragmentation or reaction mode of operation wherein ions are substantially fragmented or reacted upon entering the collision, fragmentation or reaction device and a relatively low fragmentation or reaction mode of operation wherein substantially fewer ions are fragmented or reacted or wherein substantially no ions are fragmented or reacted upon entering the collision, fragmentation or reaction device. According to an embodiment in the relatively high fragmentation or reaction mode of operation ions entering the collision, fragmentation or reaction device are accelerated through a potential difference selected from the group consisting of: (i) $\geq 10$ V; (ii) $\geq 20$ V; (iii) $\geq 30$ V; (iv) $\geq 40$ V; (v) $\geq 50$ V; (vi) $\geq 60$ V; (vii) $\geq 70$ V; (viii) $\geq 80$ V; (ix) $\geq 90$ V; (x) $\geq 100$ V; (xi) $\geq 110$ V; (xii) $\geq 120$ V; (xiii) $\geq 130$ V; (xiv) $\geq 140$ V; (xv) $\geq 150$ V; (xvi) $\geq 160$ V; (xvii) $\geq 170$ V; (xviii) $\geq 180$ V; (xix) $\geq 190$ V; and (xx) $\geq 200$ V. According to an embodiment in the relatively low fragmentation or reaction mode of operation ions entering the collision, fragmentation or reaction device are accelerated through a potential difference selected from the group consisting of: (i) $\leq 20$ V; (ii) $\leq 15$ V; (iii) $\leq 10$ V; (iv) $\leq 5$V; and (v) $\leq 1$V.

The control system is preferably arranged and adapted to switch the collision, fragmentation or reaction device between the relatively high fragmentation or reaction mode of operation and the relatively low fragmentation or reaction mode of operation at least once every 1 ms, 5 ms, 10 ms, 15 ms, 20 ms, 25 ms, 30 ms, 35 ms, 40 ms, 45 ms, 50 ms, 55 ms, 60 ms, 65 ms, 70 ms, 75 ms, 80 ms, 85 ms, 90 ms, 95 ms, 100 ms, 200 ms, 300 ms, 400 ms, 500 ms, 600 ms, 700 ms, 800 ms, 900 ms, 1 s, 2 s, 3 s, 4 s, 5 s, 6 s, 7 s, 8 s, 9 s or 10 s.

The collision, fragmentation or reaction device is preferably arranged and adapted to receive a beam of ions and to convert or partition the beam of ions such that at least 1, 2, 3, 4, 5, 6, 7, 8, 9, 10, 11, 12, 13, 14, 15, 16, 17, 18, 19 or 20 separate groups or packets of ions are confined and/or isolated in the collision, fragmentation or reaction device at any particular time, and wherein each group or packet of ions is preferably separately confined and/or isolated in a separate axial potential well formed in the collision, fragmentation or reaction device.

The first mass to charge ratio filter or mass to charge ratio mass analyser is preferably arranged upstream and/or downstream of the ion mobility spectrometer or separator. The first mass to charge ratio filter or mass to charge ratio analyser is preferably selected from the group consisting of: (i) a quadrupole rod set mass filter; (ii) a Time of Flight mass filter or mass analyser; (iii) a Wein filter; and (iv) a magnetic sector mass filter or mass analyser.

The mass spectrometer preferably further comprises an ion guide, ion trap or ion trapping region arranged upstream and/or downstream of the ion mobility spectrometer or separator. The ion guide, ion trap or ion trapping region is preferably arranged to trap, store or accumulate ions and then preferably to periodically pulse ions out from the ion guide, ion trap or ion trapping region into or towards the ion mobility spectrometer or separator.

The mass spectrometer preferably further comprises a second mass to charge ratio filter or mass to charge ratio analyser. The second mass to charge ratio filter or mass to charge ratio analyser is preferably arranged upstream and/or downstream of the collision, fragmentation or reaction device.

The second mass to charge ratio filter or mass to charge ratio analyser is preferably selected from the group consisting of: (i) a quadrupole rod set mass filter; (ii) a Time of Flight mass filter or mass analyser; (iii) a Wein filter; and (iv) a magnetic sector mass filter or mass analyser.

According to an embodiment the mass spectrometer preferably further comprises an ion source. The ion source is preferably selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; and (xvii) a Thermospray ion source.

The mass spectrometer preferably comprises a continuous or pulsed ion source.

According to an embodiment a mass analyser is preferably arranged upstream and/or downstream of the collision, fragmentation or reaction device. The mass analyser is preferably selected from the group consisting of: (i) a Fourier Transform ("FT") mass analyser; (ii) a Fourier Transform Ion Cyclotron Resonance ("FTICR") mass analyser; (iii) a Time of Flight ("TOF") mass analyser; (iv) an orthogonal acceleration Time of Flight ("oaTOF") mass analyser; (v) an axial acceleration Time of Flight mass analyser; (vi) a magnetic sector mass spectrometer; (vii) a Paul or 3D quadrupole mass analyser; (viii) a 2D or linear quadrupole mass analyser; (ix) a Penning trap mass analyser; (x) an ion trap mass analyser; (xi) a Fourier Transform orbitrap; (xii) an electrostatic Ion Cyclotron Resonance mass spectrometer; (xiii) an electrostatic Fourier Transform mass spectrometer; and (xiv) a quadrupole rod set mass filter or mass analyser.

According to another aspect of the present invention there is provided a method of mass spectrometry comprising:

transmitting parent or precursor ions having mass to charge ratios within a first range;

providing an ion mobility spectrometer or separator;

providing an attenuation means for attenuating or diverting ions in a mode of operation;

providing a collision, fragmentation or reaction device; and controlling the operation of the attenuation means so that ions having mass to charge ratios within the first range but having one or more first undesired charge states are substantially attenuated.

According to another aspect of the present invention there is provided a mass spectrometer comprising:

the combination of an ion mobility spectrometer or separator and an ion attenuation means; and a collision, fragmentation or reaction device;

wherein in a mode of operation only parent or precursor ions having both a specific mass to charge ratio and a specific charge state are onwardly transmitted by the combination to the collision, fragmentation or reaction device.

Preferably, in the mode of operation doubly or multiply charged parent or precursor ions are onwardly transmitted by the combination whereas singly charged parent or precursor ions are substantially attenuated by the combination.

According to another aspect of the present invention there is provided a method of mass spectrometry comprising:

providing the combination of an ion mobility spectrometer or separator and an ion attenuation means;

providing a collision, fragmentation or reaction device; and operating the combination so that only parent or precursor ions having both a specific mass to charge ratio and a specific charge state are onwardly transmitted to the collision, fragmentation or reaction device.

Preferably, doubly or multiply charged parent or precursor ions are onwardly transmitted by the combination whereas singly charged parent or precursor ions are substantially attenuated by the combination.

According to the preferred embodiment a method of selective ion monitoring is provided wherein ions are preferably separated according to both their mass to charge ratio and their charge (z) prior to their decomposition in a collision cell or fragmentation in another device. One or more specific fragment, daughter or product ions resulting from the decomposition process are then preferably subsequently separated according to their mass to charge ratio and detected. The preferred embodiment relates to an improved method of Multiple Reaction Monitoring.

According to the preferred embodiment parent or precursor ions having a specific mass to charge ratio are preferably selected and onwardly transmitted by a first mass to charge ratio filter. The parent or precursor ions are then preferably temporally separated in an ion mobility separator or spectrometer. According to the preferred embodiment, parent or precursor ions having a specific desired charge (z) exit the ion mobility spectrometer or separator and are then onwardly transmitted by an ion gate to a gas collision cell. The parent or precursor ions having the desired charge state are preferably fragmented in the gas collision cell. However, other ions which have substantially the same mass to charge ratio as the parent or precursor ions of interest but which have a charge state different to the parent or precursor ions of interest preferably emerge from the ion mobility spectrometer or separator at a different time. These undesired ions are preferably attenuated by the ion gate.

Daughter, fragment, product or adduct ions formed within the gas collision cell are preferably onwardly transmitted from the gas collision cell to a second mass to charge ratio filter or mass to charge ratio analyser which is preferably arranged downstream of the gas collision cell. The second mass to charge ratio filter or mass to charge ratio analyser is preferably scanned and the ions transmitted by the second mass to charge ratio filter or mass to charge ratio analyser are preferably detected by an ion detector which is preferably arranged downstream of the second mass to charge ratio filter or mass to charge ratio analyser.

Ions in the ion mobility spectrometer or separator are preferably subjected to an electric field in the presence of a buffer gas. Different species of ion preferably acquire different velocities and hence become temporally separated according to their ion mobility. The mobility of an ion in an ion mobility spectrometer or separator preferably depends upon its size, shape and charge.

The first mass to charge ratio filter and/or the second mass to charge ratio filter preferably comprise a quadrupole rod set mass to charge ratio filter. However, other types of mass to charge ratio filter are also contemplated according to other less preferred embodiments. The mass filter may comprise a multi-pole rod set, a quadrupole mass filter, a Time of Flight mass spectrometer, a Wein filter, or a magnetic sector mass analyser.

According to another embodiment ions are temporally separated in an ion mobility spectrometer or separator and ions are onwardly transmitted to a mass to charge ratio filter which is arranged downstream of the ion mobility spectrometer or separator. The mass to charge ratio filter selects ions having a particular mass to charge ratio and an ion gate in combination with the ion mobility spectrometer or separator selects ions having a particular charge state. Ions which are onwardly transmitted are then passed to a collision cell where the ions are preferably fragmented. According to a preferred embodiment fragment ions having one or more specific mass to charge ratios are preferably transmitted by a second mass to charge filter and are preferably detected by an ion detector.

The preferred embodiment preferably relates to selecting ions according to both their mass to charge ratio (m/z) and also according to their charge (z) state prior to fragmenting the ions. This approach provides greater selectivity than merely selecting ions according to their mass to charge ratio prior to fragmenting the ions.

The preferred embodiment is particularly advantageous in combination with ionisation methods such as Electrospray ionisation wherein analyte ions of interest produced by the ion source will be predominantly multiply charged. The ions produced by Electrospray ionisation of proteins and peptides will normally be multiply charged whilst ions resulting from chemical matrix material will normally be singly charged. As a result, the extra selectivity of further filtering ions having a particular mass to charge ratio according to charge state (z) provides an important advantage since it enables singly charged background ions to be filtered out. According to the preferred embodiment chemical matrix material which would otherwise interfere with or otherwise even totally obscure analyte ions of interest can effectively be removed.

An RF ion guide may be provided upstream of the ion mobility spectrometer or separator. The ion guide or other trapping region may be used to accumulate and store ions. The ions may then be released as packets of ions in pulses. A plate or electrode may, for example, be arranged at the exit of the ion guide, ion trap or ion trapping region. The plate or electrode may in one embodiment be set to or maintained at a voltage such as to form a potential barrier thereby preventing ions from exiting the ion guide, ion trap or trapping region. For positive ions, a potential of about +10 volts with respect to the potential of the electrodes forming the ion guide, ion trap or ion trapping region may be used. A similar plate or electrode may also be provided at the entrance to the ion guide, ion trap or ion trapping region. The plate or electrode may be maintained at a similar potential to the plate or electrode arranged at the exit of the ion guide, ion trap or ion trapping region and may be arranged to prevent ions from exiting the ion guide, ion trap or ion trapping region via the entrance. If the potential on the plate or electrode arranged at the exit of the ion guide, ion trap or ion trapping region is momentarily lowered to 0 volts, or less than 0 volts, with respect to the potential at which the electrodes forming the ion guide, ion trap or ion trapping region are held, then ions will be released from the ion guide, ion trap or ion trapping region in a pulse. The release of a pulse of ions into the ion mobility separator or spectrometer preferably marks the start of an ion mobility separation experiment or ion mobility separation cycle.

The ion mobility spectrometer or separator may comprise a drift tube or cell wherein an axial electric field is provided or maintained in the presence of a buffer gas. The axial electric field will preferably result in ions having a relatively high ion mobility passing faster than ions having a relatively low ion mobility thereby causing a separation of ions according to their ion mobility. The drift cell may also act as an ion guide wherein ions are radially confined within the drift cell by the application of an inhomogeneous RF electric field to electrodes forming the drift cell.

According to another embodiment, an ion mobility spectrometer or separator may be provided wherein ions are radially confined by an inhomogeneous RF field in an ion guide. Ions are preferably propelled forward by a potential hill or barrier that preferably moves along the axis of the ion guide in the presence of a buffer gas. Appropriate selection of the amplitude and velocity of the travelling potential barrier, and the type and pressure of gas, allows ions to slip selectively over the potential barrier according to their ion mobility. This in turn allows ions having different ion mobilities to be transported at different velocities and hence to be separated according to their ion mobility.

The cycle time for an ion mobility separation experiment according to a preferred embodiment may be between 2 and 50 ms, and more typically between 5 and 20 ms. A cycle time of about 10 ms is particularly preferred. Ions exiting the ion mobility spectrometer or separator are preferably detected and recorded. The ion mobility cycle is then preferably repeated.

Ions having substantially the same mass to charge ratio but having different charge states will arrive at the exit of the ion mobility spectrometer or separator at substantially different times. Ions having a relatively high charge state will arrive at the exit of the ion mobility spectrometer or separator before ions having substantially the same mass to charge ratio but a relatively low charge state. The ion mobility spectrometer or separator thereby allows ions having a required or desired charge state to be onwardly transmitted by an attenuation means whilst other ions may be discarded prior to the gas collision cell or other fragmentation device. Ions may according to one embodiment be discarded or attenuated by operating an ion gate arranged between the exit of the ion mobility spectrometer or separator and the entrance to the gas collision cell. At one or more appropriate time or times during the course of an ion mobility experiment the ion gate may be set to allow the transmission of ions having the required or a desired charge state. The ion gate is preferably also operated so as to attenuate ions at other times which have an undesired charge state.

According to an embodiment singly charged ions (or ions having other charge states) may be discarded or attenuated by temporarily removing an AC or RF voltage applied to the ion mobility spectrometer or separator once doubly or multiply charged ions have exited the ion mobility spectrometer or separator. When the AC or RF voltage is removed, ions are preferably no longer confined radially within the ion mobility spectrometer or separator and hence are allowed to disperse. Singly charged ions having a specific mass to charge ratio will be the last ions to arrive at the exit of the ion mobility spectrometer or separator. Hence, as soon as doubly or multiply charged ions having substantially the same mass to charge ratio exit from the ion mobility spectrometer or separator the radially confining AC or RF voltage may be removed temporarily. As a result, undesired singly charged ions are no longer confined radially within the ion mobility spectrometer or separator and hence are allowed to become dispersed and become lost to the system.

Ions are preferably received by, and fragmented in, a gas collision cell. The collision cell is preferably maintained at a pressure between $10^{-4}$ mbar and 1 mbar, or more preferably between $10^{-3}$ and $10^{-1}$ mbar. The collision cell preferably comprises an RF ion guide which confines ions close to the central axis. The ions preferably remain close to the central axis when undergoing collisions with background gas molecules. The collision cell may comprise a multi-pole rod set ion guide wherein an AC or RF voltage or potential is applied between neighbouring rods. Alternatively, the collision cell may comprise a ring stack ion guide wherein an AC or RF voltage or potential is applied between neighbouring rings. Other embodiments are contemplated wherein the collision cell may comprise a different form of RF ion guide. Ions entering the collision cell with an energy of at least 10 eV are preferably arranged to undergo multiple collisions with gas molecules and hence are preferably induced to fragment.

Other less preferred embodiments are contemplated wherein the collision cell may comprise an Electron Capture Dissociation fragmentation device, an Electron Transfer Dissociation fragmentation device or a Surface Induced Dissociation fragmentation device.

The mass spectrometer preferably further comprises a second mass to charge ratio filter arranged downstream of the gas collision cell and upstream of the ion detector. The second mass to charge ratio filter is preferably arranged to transmit ions having a single mass to charge ratio or ions having a range of mass to charge ratios. The second mass to charge ratio filter preferably comprises a quadrupole rod set mass to charge ratio filter. According to other less preferred embodiments the second mass to charge ratio filter may comprise a Time of Flight mass spectrometer, a Wein filter or a magnetic sector mass analyser.

According to other less preferred embodiments the second mass to charge ratio filter or mass to charge ratio analyser may comprise an axial acceleration Time of Flight mass analyser, an orthogonal acceleration Time of Flight mass analyser, a 3D quadrupole ion trap, a linear quadrupole ion trap, a magnetic sector mass analyser, an ion cyclotron resonance mass analyser, an orbitrap mass analyser, or any combination thereof.

An ion source is preferably provided which preferably comprises a pulsed ion source such as a Laser Desorption Ionisation ("LDI") ion source, a Matrix Assisted Laser Desorption Ionisation ("MALDI") ion source or a Desorption Ionisation on Silicon ("DIOS") ion source.

Alternatively, a continuous ion source may be provided. The continuous ion source may comprise an Electrospray Ionisation ("ESI") ion source, an Atmospheric Pressure Chemical Ionisation ("APCI") ion source, an Electron Impact ("EI") ion source, an Atmospheric Pressure Photon Ionisation ("APPI") ion source, a Chemical Ionisation ("CI") ion source, a Fast Atom Bombardment ("FAB") ion source, a Liquid Secondary Ion Mass Spectrometry ("LSIMS") ion source, a Field Ionisation ("FI") ion source or a Field Desorption ("FD") ion source. Other continuous or pseudo-continuous ion sources may also be used.

BRIEF DESCRIPTION OF THE DRAWINGS

Various embodiments of the present invention together with an arrangement given for illustrative purposes only will now be described, by way of example only, and with reference to the accompanying drawings in which:

FIG. 5A shows a mass spectrum resulting from the tryptic digest of the protein β-lactoGlobulin over the mass to charge ratio range 730 to 810 obtained conventionally and FIG. 5B shows a corresponding mass spectrum obtained by removing singly charged ions which result from background chemical matrix according to an embodiment of the present invention.

DETAILED DESCRIPTION OF THE PREFERRED EMBODIMENTS

Figure 1:
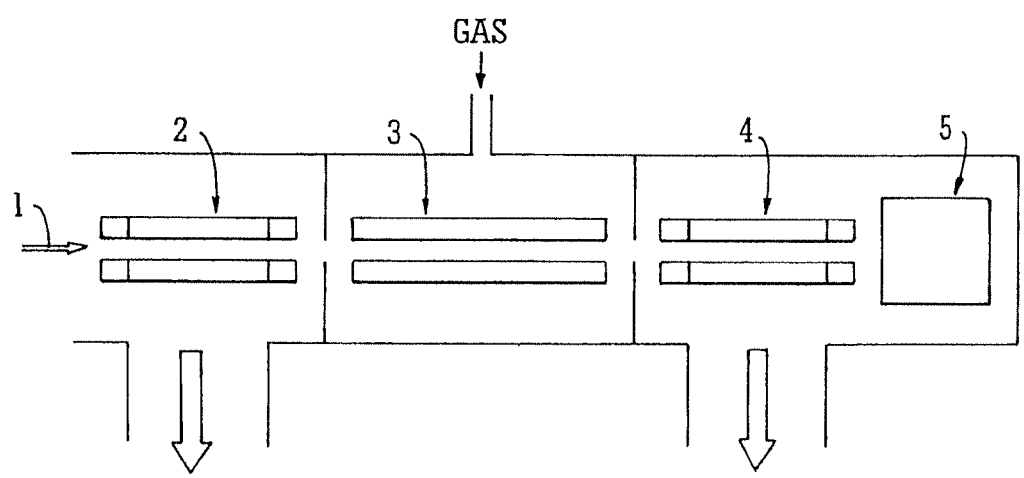
FIG. 1 illustrates a conventional triple quadrupole mass spectrometer.

A conventional triple quadrupole mass spectrometer arrangement is shown in FIG. 1. According to this arrangement, a beam of ions 1 is received by a first quadrupole mass to charge ratio filter 2. Parent ions having a mass to charge ratio of interest are onwardly transmitted by the first quadruple mass to charge ratio filter 2 and are transmitted to and received by a gas collision cell 3 arranged downstream of the first quadrupole mass to charge ratio filter 2. Parent ions in the gas collision cell 3 are arranged to undergo multiple collisions with background gas molecules and are induced to fragment into fragment or daughter ions. The resulting fragment or daughter ions (and any remaining unfragmented parent or precursor ions) then pass from the gas collision cell 3 to a second quadrupole mass to charge ratio filter or mass to charge ratio analyser 4 which is arranged downstream of the gas collision cell 3. The second quadrupole mass to charge ratio filter or mass to charge ratio analyser 4 may be scanned and ions transmitted by the second quadrupole mass to charge ratio filter or mass to charge ratio analyser 4 are detected by an ion detector 5 which is arranged downstream of the second quadrupole mass to charge ratio filter or mass to charge analyser 4.

The first quadrupole mass to charge ratio filter 2 and the second quadrupole mass to charge ratio filter 4 are typically operated in a mode of operation wherein they are arranged to transmit ions having a single or specific mass to charge ratio. The first quadrupole mass to charge ratio filter 2 and the second quadrupole mass to charge ratio filters 4 will therefore have a 100% duty cycle when used to transmit ions having a single or specific mass to charge ratio.

It is known to operate the conventional triple quadrupole mass spectrometer in a Selected Reaction Monitoring (SRM) mode of operation wherein a single species of parent or precursor ions is arranged to be transmitted by the first quadrupole mass to charge ratio filter 2. Similarly, a single species of fragment or daughter ion is arranged to be transmitted by the second quadrupole mass to charge ratio filter 4 arranged downstream of the collision cell 3. A triple quadrupole mass spectrometer when operated in a SRM mode of operation is very specific and exceptionally sensitive. Triple quadrupole mass spectrometers have found significant use in the drug discovery and development process where they may be used in either a SRM mode of operation or a related MRM (Multiple Reaction Monitoring) mode of operation to quantify target compounds.

Figure 2:
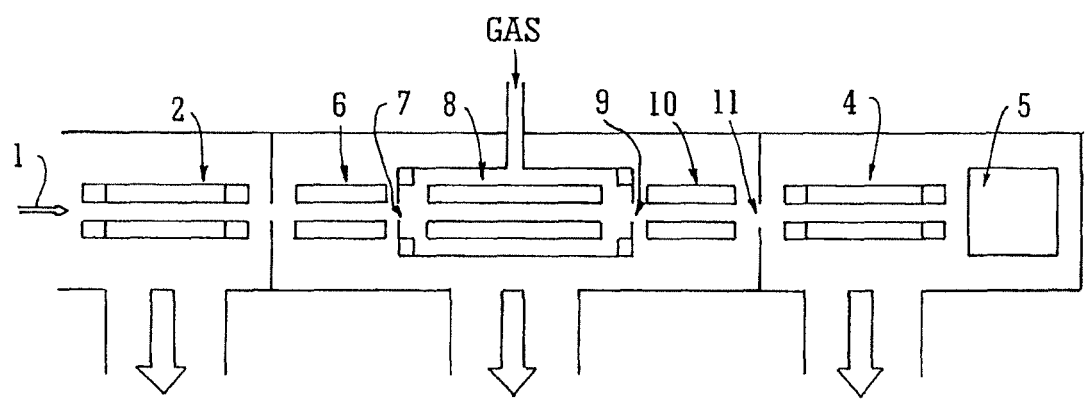
FIG. 2 shows a mass spectrometer according to an embodiment of the present invention wherein an ion gate is provided downstream of an ion mobility spectrometer or separator to selectively transmit parent ions having a desired charge state to a collision cell.

FIG. 2 shows a mass spectrometer according to a preferred embodiment of the present invention. The mass spectrometer preferably comprises a continuous ion source (e.g. an Electrospray ion source) which preferably generates a beam of ions 1. The beams of ions 1 is preferably passed to a first mass to charge ratio filter or mass to charge ratio analyser 2. The first mass to charge ratio filter or mass to charge ratio analyser 2 preferably comprises a quadrupole rod set mass to charge ratio filter. According to another less preferred embodiment other types of mass filter may also be used. The first mass to charge ratio filter or mass to charge ratio analyser 2 may be operated in a non-resolving or RF-only mode of operation according to a less preferred embodiment wherein substantially all ions are onwardly transmitted. However, alternatively, and more preferably, the first mass to charge ratio filter or mass to charge ratio analyser 2 is preferably operated in a mass filtering mode of operation wherein only ions having a specific mass to charge ratio or ions having mass to charge ratios within a specific range are onwardly transmitted by the first mass to charge ratio filter or mass to charge ratio analyser 2.

Ions which are onwardly transmitted by the first mass to charge ratio filter or mass to charge ratio analyser 2 are preferably accumulated and trapped in an ion guide, ion trapping region or ion trap 6 which is preferably arranged downstream of the first mass to charge ratio filter and upstream of an ion mobility spectrometer or separator 8. Ions are preferably confined within the ion guide, ion trapping region or ion trap 6 for a period of time by applying a relatively high voltage or potential V2 to a first ion gate 7 which is preferably arranged downstream of the ion guide, ion trapping region or ion trap 6. Ions are preferably periodically pulsed out of the ion guide, ion trapping region or ion trap 6 by applying an extraction voltage to the first ion gate 7.

The ion guide, ion trapping region or ion trap 6 may according to one embodiment comprise a quadrupole or other multi-pole rod set ion guide. The ion guide, ion trapping region or ion trap 6 preferably has a length of approximately 75 mm.

According to another embodiment the ion guide, ion trapping region or ion trap 6 may comprise an ion tunnel ion guide or ion tunnel ion trap. The ion tunnel ion guide or ion tunnel ion trap preferably comprises a plurality of electrodes having apertures through which ions are preferably transmitted in use. The apertures are preferably all the same size.

However, according to other embodiments, at least 50%, 55%, 60%, 65%, 70%, 75%, 80%, 85%, 90% or 95% of the electrodes preferably have apertures which are substantially the same size. The ion tunnel ion guide or ion tunnel ion trap may according to an embodiment comprise approximately 50 electrodes. Adjacent electrodes are preferably connected to opposite phases of an AC or RF voltage supply so that ions are radially confined, in use, within the ion tunnel ion guide or ion tunnel ion trap by a radial pseudo-potential well.

The AC or RF voltage applied to the electrodes of the ion guide, ion trapping region or ion trap 6 preferably has a frequency within the range 0.1-3.0 MHz, further preferably 0.3-2.0 MHz. A frequency within the range 0.5-1.5 MHz is particularly preferred.

The electrodes comprising the ion guide, ion trapping region or ion trap 6 are preferably maintained at a first DC voltage or potential V1. The first ion gate 7 at the exit region of the ion guide, ion trapping region or ion trap 6 is preferably held for a majority of the time at a second DC voltage or potential V2 which is preferably higher than the first DC voltage or potential V1 at which the electrodes comprising the ion guide, ion trapping region or ion trap 6 are preferably maintained. The voltage or potential applied to the first ion gate 7 is preferably dropped periodically to a third DC voltage or potential V3 which is preferably lower than the first DC voltage or potential V1 at which the electrodes comprising the ion guide, ion trapping region or ion trap 6 are preferably maintained. Ions are therefore preferably caused to be accelerated out of the ion guide, ion trapping region or ion trap 6 when the first ion gate 7 is maintained at the third DC voltage or potential V3. The ions are preferably accelerated towards and admitted into the ion mobility spectrometer or separator 8 which is preferably arranged downstream of the ion guide, ion trapping region or ion trap 6.

The voltage or potential applied to the first ion gate 7 is preferably only dropped for a relatively short period of time so that the ions which are ejected out from the ion guide, ion trapping region or ion trap 6 are preferably ejected in a substantially pulsed manner. Accordingly, a pulse of ions is preferably transmitted to and received by the ion mobility spectrometer or separator 8.

According to a less preferred embodiment the ion source may comprise a pulsed ion source such as a Matrix Assisted Laser Desorption Ionisation ("MALDI") ion source or a Laser Desorption Ionisation ion source instead of a continuous ion source. If a pulsed ion source is provided then the ion guide, ion trapping region or ion trap 6 and/or the first ion gate 7 may be omitted so that ions are according to one embodiment directly pulsed from the ion source into the ion mobility spectrometer or separator 8.

According to an embodiment the ion guide, ion trapping region or ion trap 6 may comprise a RF ring stack ion guide wherein a plurality of electrodes having apertures is provided. A superimposed travelling wave may be applied to the electrodes of the ion guide, ion trapping region or ion trap 6 so that one or more transient DC voltages or potentials or one or more transient DC voltage or potential waveforms are preferably applied to the electrodes forming the ion guide, ion trapping region or ion trap 6. The one or more transient DC voltages or potentials or the one or more transient DC voltage or potential waveforms which are preferably applied to the electrodes of the ion guide, ion trapping region, or ion trap 6 preferably urge ions along the length of the ion guide, ion trapping region or ion trap 6. The apertures of the electrodes forming the ion guide, ion trapping region or ion trap 6 are preferably all the same size. Adjacent electrodes are preferably connected to opposite phases of an AC or RF voltage supply. One or more transient DC voltages or potentials or one or more transient DC voltage or potential waveforms are preferably applied to the electrodes so that one or more potential hills or barriers are created which are preferably translated along the length of the ion guide, ion trapping region or ion trap 6. The one or more transient DC voltages or potentials or the one or more transient DC voltage or potential waveforms are preferably progressively applied to a succession of electrodes such that one or more potential hills or barriers preferably move along the axis of the ion guide, ion trapping region or ion trap 6 in the direction in which the ions are to be propelled or driven.

The ion guide, ion trapping region or ion trap 6 is preferably provided in a vacuum chamber which is preferably maintained, in use, at a pressure within the range $10^{-3}$ mbar to $10^{-1}$ mbar. According to less preferred embodiments, the vacuum chamber may be maintained at a pressure greater than $10^{-1}$ mbar up to a pressure at or near 1 mbar. According to other less preferred embodiments, the vacuum chamber may alternatively be maintained at a pressure below $10^{-3}$ mbar. The gas pressure in the ion guide, ion trapping region or ion trap 6 is preferably sufficient to impose collisional damping of ion motion but is preferably insufficient so as to cause or impose excessive viscous drag on the movement of ions. The amplitude and average velocity of the one or more potential hills or barriers applied to the ion guide, ion trapping region or ion trap 6 is preferably set such that ions will not slip over a potential hill or barrier as it is translated along the length of the ion guide, ion trapping region or in trap 6. The ions are preferably transported ahead of each travelling potential hill or barrier regardless of their mass, mass to charge ratio or ion mobility.

Ions are preferably transported along and through the ion guide, ion trapping region or ion trap 6 and are preferably released in packets or groups in a substantially pulsed manner into or towards the ion mobility spectrometer or separator 8. The wave cycle time of the one or more transient DC voltages or potentials or the one or more transient DC voltage or potential waveforms applied to the ion guide, ion trapping region or ion trap 6 may according to one embodiment be arranged substantially to equal the cycle time of the ion mobility spectrometer or separator 8. Alternatively, ions may be accumulated and held in a trapping region near the exit of the ion guide, ion trapping region or ion trap 6. The ions may then be arranged to be released to the ion mobility spectrometer or separator 8 at the start of each cycle of operation of the ion mobility spectrometer or separator 8. In this mode of operation the wave cycle time of ion guide, ion trapping region or ion trap 6 may not necessarily match the cycle time of the ion mobility spectrometer or separator 8.

The ion mobility spectrometer or separator 8 is preferably arranged to cause ions to become temporally separated according to their ion mobility as they pass along the length of the ion mobility spectrometer or separator 8.

The ion mobility spectrometer or separator 8 may comprise a drift tube having a number of guard rings distributed within the drift tube. The guard rings are preferably interconnected by equivalent valued resistors and are preferably connected to a DC voltage source. A linear DC voltage gradient is preferably generated or provided along the length of the drift tube in use. The guard rings are preferably not connected to an AC or RF voltage source and hence ions preferably are not radially confined within the ion mobility spectrometer or separator 8.

According to another more preferred embodiment the ion mobility spectrometer or separator 8 may comprise a plurality of ring, annular or plate electrodes. Each electrode preferably comprises an aperture therein through which ions are preferably transmitted in use. The apertures are preferably all the same size and are preferably circular. According to other embodiments at least 50%, 55%, 60%, 65%, 70%, 75%, 80%, 85%, 90% or 95% of the electrodes have apertures which are substantially the same size or area.

According to an embodiment the ion mobility spectrometer or separator 8 may have a length in the range of 100-200 mm.

The ion mobility spectrometer or separator 8 preferably comprises a plurality of electrodes arranged in a vacuum chamber. The ion mobility spectrometer or separator 8 is preferably provided in a vacuum chamber which is preferably maintained, in use, at a pressure within the range 0.1-10 mbar. According to less preferred embodiments, the vacuum chamber may be maintained at a pressure greater than 10 mbar up to a pressure at or near atmospheric pressure. According to other less preferred embodiments the vacuum chamber may be maintained at a pressure below 0.1 mbar.

Alternate electrodes forming the ion mobility spectrometer or separator 8 are preferably coupled to opposite phases of an AC or RF voltage supply. The AC or RF voltage supply preferably has a frequency within the range 0.1-3.0 MHz, preferably 0.3-2.0 MHz. A frequency in the range 0.5-1.5 MHz is particularly preferred. The AC or RF voltage applied to the electrodes forming the ion mobility spectrometer or separator 8 preferably results in a radial pseudo-potential well being created which preferably acts to confine ions radially within the ion mobility spectrometer or separator 8.

The electrodes forming the ion guide, ion trapping or ion trap 6 and the electrodes forming the ion mobility spectrometer or separator 8 may according to one embodiment be interconnected via resistors to a DC voltage supply. The DC voltage supply may, for example, comprise a 400 V supply. The resistors interconnecting the electrodes forming the ion mobility spectrometer or separator 8 may be arranged to be substantially equal in value so that a substantially linear axial DC voltage gradient is preferably maintained or generated along the length of the ion mobility spectrometer or separator 8. Other embodiments are contemplated wherein a DC voltage gradient may be maintained or generated along the length of the ion mobility spectrometer or separator 8 which may have a non-linear or stepped profile. The AC or RF voltage which is preferably applied to the electrodes of the ion mobility spectrometer or separator 8 is preferably superimposed upon the DC voltage which is preferably otherwise applied to the electrodes.

The second and third DC voltages or potentials V2,V3 which are preferably applied to the first ion gate 7 may be arranged to float on the DC voltage supply. The AC or RF voltage supply is preferably isolated from the DC voltage supply by a capacitor.

According to an embodiment one or more transient DC voltages or potentials or one or more transient DC voltage or potential waveforms may be applied to one or more of the electrodes forming the ion mobility spectrometer or separator 8 in order to urge ions along the length of the ion mobility spectrometer or separator 8. The one or more transient DC voltages or potentials or the one or more transient DC voltage or potential waveforms preferably result in one or more potential hills or barriers being created which are then caused to move along the length of the ion mobility spectrometer or separator 8. The one or more transient DC voltages or potentials or the one or more transient DC voltage or potential waveforms are preferably progressively applied to a succession of electrodes such that one or more potential hills or barriers move along the length of the ion mobility spectrometer or separator 8 in the direction in which the ions are to be propelled or driven.

The presence of gas within the ion mobility spectrometer or separator 8 preferably imposes a viscous drag on the movement of ions. The amplitude and average velocity of the one or more potential hills or barriers which are preferably translated along the length of the ion mobility spectrometer or separator 8 is preferably set such that at least some ions will periodically slip over a potential hill or barrier as the potential hill or barrier is translated along the length of the ion mobility spectrometer or separator 8. The lower the mobility of an ion, the more likely the ion will be to slip over a potential hill or barrier. This effect allows ions having different ion mobilities to be transported at different velocities along the length of the ion mobility spectrometer or separator 8. Ions will therefore become temporally separated according to their ion mobility.

Typical drift times of ions through the ion mobility spectrometer or separator 8 are of the order of a several milliseconds. After all desired ions have traversed the ion mobility spectrometer or separator 8 a new pulse of ions is preferably admitted into the ion mobility spectrometer or separator 8. This preferably marks the start of a new cycle of operation of the ion mobility spectrometer or separator 8. Many cycles of operation of the ion mobility spectrometer or separator 8 may be performed during an experimental run.

Ions having different mobilities preferably arrive at the exit of the ion mobility spectrometer or separator 8 at substantially different times. Ions having substantially the same mass to charge ratio but having different charge states will also arrive at the exit of the ion mobility spectrometer or separator 8 at substantially different times. Ions having a certain mass to charge ratio and a relatively high charge state will arrive at the exit of the ion mobility spectrometer or separator 8 prior to ions having substantially the same mass to charge ratio but a relatively low charge state.

According to a particularly preferred embodiment of the present invention a second ion gate 9 is arranged at the exit of or downstream of the ion mobility spectrometer or separator 8. Ions having one or more specific or desired charge states which emerge at the exit of the ion mobility spectrometer or separator 8 are preferably onwardly transmitted whilst other ions having undesired charge states are preferably discarded, attenuated or diverted by activating the second ion gate 9 in a substantially synchronised manner with the operation of the ion mobility spectrometer or separator 8 and the emergence of ions from the ion mobility spectrometer or separator 8.

Although the second ion gate 9 is preferably positioned at the exit of the ion mobility spectrometer or separator 8, other embodiments are contemplated wherein the second ion gate 9 may be arranged further downstream, for example, at the entrance to a gas collision cell 10 which is also preferably provided downstream of the ion mobility spectrometer or separator 8. The second ion gate 9 is preferably actuated at appropriate times during the course of an ion mobility spectrum so as to allow the onward transmission only of those ions having a desired charge state.

The first ion gate 7 and/or the second ion gate 9 may comprise a set of electrodes or one or more electrodes or other devices that provide a deflection field in order to deflect undesired ions out of an ion transmission path. Alternatively, the first ion gate 7 and/or the second ion gate 9 may comprise a set of electrodes or one or more electrodes or other devices that provide a potential barrier that substantially prevents or attenuates ions from being onwardly transmitted at a particular instance in time.

The first ion gate 7 and/or the second ion gate 9 may be arranged so that when they are energised they substantially prevent ions from being onwardly transmitted and when they are de-energised they substantially allow ions to be onwardly transmitted. Alternatively, the first ion gate 7 and/or the second ion gate 9 may be arranged so that they substantially prevent ions from being onwardly transmitted when they are de-energised and so that they allow ions to be onwardly transmitted when they are energised. Various alternative ways of selectively onwardly transmitting desired ions having desired charge state(s) and/or attenuating or diverting undesired ions having undesired charge state(s) are also contemplated.

According to an embodiment ions may be discarded or attenuated by temporarily removing an AC or RF voltage which is preferably normally applied to one or more electrodes of the ion mobility spectrometer or separator 8 and which normally causes ions to be confined radially within the ion mobility spectrometer or separator 8. As a result, ions are preferably no longer confined radially in at least a portion of the ion mobility spectrometer or separator 8 and hence the ions present in the portion of the ion mobility spectrometer or separator are preferably allowed to disperse and hence become lost to the system. This approach may, in particular, be used to remove or attenuate undesired singly charged ions which are likely to correspond with undesired background ions. Singly charged ions having a specific mass to charge ratio will arrive at the exit of the ion mobility spectrometer or separator 8 after multiply charged ions having substantially the same mass to charge ratio. Hence, as soon as the last doubly charged ions of interest have exited the ion mobility spectrometer or separator 8 any means for propelling or urging ions along or through the length of the ion mobility spectrometer or separator 8 may be switched OFF or otherwise removed or reduced. Alternatively and/or in addition, at the same time the AC or RF voltage which is preferably applied to at least some of the electrodes forming the ion mobility spectrometer or separator 8 may preferably be temporarily removed from being applied to at least one or more of the electrodes forming the ion mobility spectrometer or separator 8. Other embodiments are contemplated wherein the amplitude of the AC or RF voltage applied to at least some of the electrodes is substantially reduced. As a result, singly charged ions are preferably allowed to become dispersed and hence become lost to the system. This provides a particularly effective way of filtering out and removing singly charged chemical matrix ions from doubly or multiply charged peptide or analyte ions which may have substantially the same or similar mass to charge ratios.

A differential pumping aperture is preferably provided at the entrance and/or exit of the ion mobility spectrometer or separator 8. The differential pumping aperture(s) preferably enables the ion mobility spectrometer or separator 8 to be maintained at a relatively high pressure without causing significant gas loading of other ion optical devices.

A gas collision cell 10 comprising a RF ion guide is preferably provided downstream of the ion mobility spectrometer or separator 8. A further differential pumping aperture 11 is preferably provided downstream of the gas collision cell 10. A second mass to charge ratio filter or mass to charge ratio analyser 4 and an ion detector 5 are preferably provided in a vacuum chamber arranged downstream of the further differential pumping aperture 11. The gas collision cell 10 is preferably provided in an intermediate vacuum stage between that of the ion mobility spectrometer or separator 8 and that of the second mass to charge ratio filter or mass to charge ratio analyser 4 and the ion detector 5. The gas collision cell 10 may be provided in the same vacuum stage and hence may be maintained at substantially the same pressure as that of the ion guide, ion trapping region or ion trap 6 which is preferably arranged upstream of the ion mobility spectrometer or separator 8.

The gas collision cell 10 may comprise a quadrupole or other multi-pole rod set ion guide. The gas collision cell 10 preferably has a length of approximately 75 mm. Alternatively, the gas collision cell 10 may comprise an ion tunnel ion guide comprising a plurality of electrodes having apertures therein through which ions are transmitted. The apertures of the electrodes forming the ion tunnel ion guide are preferably all the same size. According to other embodiments, at least 50%, 55%, 60%, 65%, 70%, 75%, 80%, 85%, 90% or 95% of the electrodes forming the ion tunnel ion guide have apertures which are substantially the same size. The ion tunnel ion guide may comprise approximately 50 electrodes. Adjacent electrodes are preferably connected to opposite phases of an AC or RF voltage supply so that ions are preferably radially confined in use within the ion tunnel ion guide.

According to a particularly preferred embodiment the gas collision cell 10 may comprise an ion tunnel ion guide wherein a travelling DC voltage or potential or a travelling DC wave is preferably applied to the electrodes forming the gas collision cell 10. According to the preferred embodiment one or more transient DC voltages or potentials or one or more transient DC voltage or potential waveforms are preferably applied to the electrodes of the gas collision cell 10. The one or more transient DC voltages or potentials or the one or more transient DC voltage or potential waveforms are preferably applied to one or more electrodes of the gas collision cell 10 so that one or more potential hills or barriers are preferably formed which are preferably translated along the length of the gas collision cell 10. The one or more transient DC voltages or potentials or the one or more transient DC voltage or potential waveforms are preferably progressively applied to a succession of electrodes such that one or more potential hills or barriers preferably move along the axis of the gas collision cell 10 in the direction in which the ions are to be propelled or driven.

The gas collision cell 10 is preferably provided in a vacuum chamber which is preferably maintained, in use, at a pressure within the range $10^{-3}$ mbar to $10^{-1}$ mbar. According to a less preferred embodiment, the vacuum chamber may be maintained at a pressure greater than $10^{-1}$ mbar up to a pressure at or near 1 mbar. According to other less preferred embodiments, the vacuum chamber housing the gas collision cell 10 may be maintained at a pressure below $10^{-3}$ mbar.

The gas pressure in the gas collision cell 10 is preferably sufficient to impose collisional damping of ion motion but is preferably insufficient to impose excessive viscous drag on the movement of ions. The amplitude and average velocity of the one or more potential hills or barriers which are preferably translated along the length of the gas collision cell 10 is preferably set such that ions are preferably prevented from slipping over a potential hill or barrier. The ions are preferably transported ahead of each travelling potential hill or barrier regardless of their mass, mass to charge ratio or ion mobility.

Ions are preferably arranged such that they are sufficiently energetic when they enter the gas collision cell 10 that they collide with gas molecules present in the gas collision cell 10 and as a result fragment into fragment or daughter ions. The energy of ions entering the gas collision cell 10 may be controlled, for example, by setting the level of a voltage difference experienced by the ions prior to entering the gas collision cell 10. Since the voltage difference can be switched near instantaneously, the gas collision cell 10 can, in effect, be switched between a relatively high fragmentation mode of operation and a relatively low fragmentation mode of operation.

According to an embodiment fragment or daughter ions which are formed in the gas collision cell 10 are preferably transmitted to a second mass to charge ratio filter or mass to charge ratio analyser 4 which is preferably arranged downstream of the gas collision cell 10. The second mass to charge ratio filter 4 may be arranged to transmit only ions having a specific mass to charge ratio or ions having a mass to charge ratio within a specific range. Ions which are onwardly transmitted by the second mass to charge ratio filter or mass to charge ratio analyser 4 preferably pass to an ion detector 5 which is preferably arranged downstream of the second mass to charge ratio filter or mass to charge ratio analyser 4. The second mass to charge ratio filter or mass to charge ratio analyser 4 preferably comprises a quadrupole rod set mass filter. The second mass to charge ratio filter or mass to charge ratio analyser 4 may be arranged to transmit all ions or may be arranged to transmit ions having a specific mass to charge ratio or ions having mass to charge ratios within a specific range.

According to other less preferred embodiments the second mass to charge ratio filter or mass to charge ratio analyser 4 may comprise an axial acceleration Time of Flight mass analyser, an orthogonal acceleration Time of Flight mass analyser, a 3D quadrupole ion trap, a linear quadrupole ion trap, a magnetic sector mass analyser, an ion cyclotron resonance mass analyser or an orbitrap mass analyser. The mass analyser may employ Fourier transforms of mass dependent resonance frequencies.

Transmission of a specific fragment or daughter ion through the second mass to charge ratio filter or mass to charge ratio analyser 4 and to the ion detector 5 preferably allows the monitoring of a specific precursor ion, based on its mass to charge ratio, its charge (z) and the mass to charge ratio of a corresponding daughter or fragment ion. This can provide additional specificity to the measurement of ions in either a SRM or a MRM mode of operation.

The pressure in the ion guide, ion trapping region or ion trap 6 preferably arranged upstream of the ion mobility spectrometer or separator 8 may be arranged to be substantially the same as the pressure in the gas collision cell 10 preferably arranged downstream of the ion mobility spectrometer or separator 8. According to a preferred embodiment both the ion guide, ion trapping region or ion trap 6 arranged upstream of the ion mobility spectrometer or separator 8 and the gas collision cell 10 arranged downstream of the ion mobility spectrometer or separator 8 are provided or arranged in the same vacuum chamber.

The ion mobility spectrometer or separator 8 is preferably contained within an inner chamber which is preferably positioned within an outer chamber which preferably contains the ion guide, ion trapping region or ion trap 6 and the gas collision cell 10. A collision gas, preferably nitrogen or argon, is preferably leaked into or provided to the inner chamber at a preferred pressure between 0.1 and 10 mbar. The collision gas is preferably allowed to leak out from the inner chamber into the outer chamber through the entrance and/or exit apertures of the inner chamber. The outer chamber is preferably pumped such as to maintain a pressure in the outer chamber within the range 0.001 and 0.01 mbar.

According to a preferred embodiment the ion guide, ion trapping region or ion trap 6, the ion mobility spectrometer or separator 8 and the gas collision cell 10 may each comprise an ion tunnel ion guide comprising a plurality of electrodes each having an electrode comprising an aperture through which ions are transmitted in use. The electrodes preferably have substantially similar sized apertures and may comprise essentially square or rectangular plates or ring electrodes. The apertures are preferably circular.

According to various embodiments, the ion guide, ion trapping region or ion trap 6 and/or the ion mobility spectrometer or separator 8 may comprise at least 10, 20, 30, 40, 50, 60, 70, 80, 90 or 100 electrodes of which at least 50%, 55%, 60%, 65%, 70%, 75%, 80%, 85%, 90% or 95% preferably have apertures which are substantially the same size or area. As will be appreciated, an ion tunnel ion guide which preferably comprises a large number of plate like electrodes is quite distinct from a multipole rod set ion guide.

According to an alternative embodiment the first mass to charge ratio filter 2 may be rearranged downstream of the ion mobility spectrometer or separator 8. According to this embodiment ions from the ion source may first be transmitted through the ion mobility spectrometer or separator 8 and may then be transmitted through the first mass to charge ratio filter in order to select ions having a specific mass to charge ratio. Ions having a specific mass to charge ratio may then be further selected according to their charge state (z). Ions may be selected according to their mass to charge ratio and their charge irrespective of the order in which the first mass to charge ratio filter 2 and the ion mobility spectrometer or separator 8 are arranged. According to this embodiment an ion gate or ion gating device which is preferably used to onwardly transmit or attenuate ions which have specific drift times through the ion mobility spectrometer or separator 8 is preferably positioned after or downstream of the ion mobility spectrometer or separator 8 and before or upstream of the gas collision cell 10. The ion gate may be positioned immediately after the ion mobility spectrometer or separator 8 and before or upstream of the first mass to charge ratio filter. In a less preferred embodiment the ion gate may be positioned after or downstream of the first mass to charge ratio filter.

Figure 3:
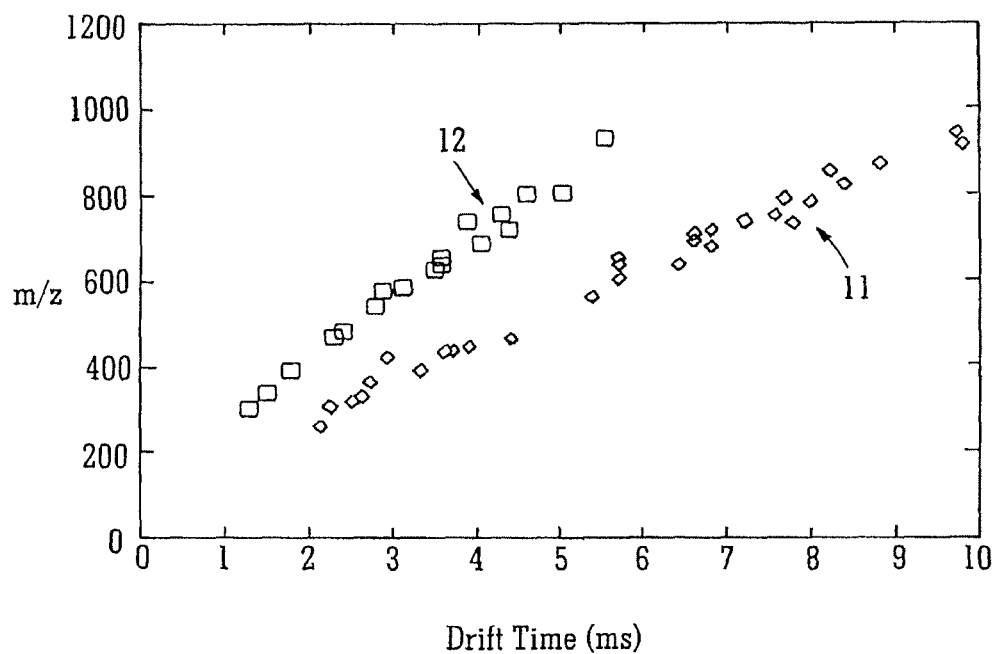
FIG. 3 shows an experimentally determined distribution of ion mobility drift time as a function of mass to charge ratio for a plurality of singly and doubly charged ions.

FIG. 3 shows a typical distribution of ion mobility drift times versus mass to charge ratio for a number of singly and doubly charged ions. The data is derived from a mixture of peptides and shows two distinct groups, one for singly charged ions 11 and one for doubly charged ions 12. For ions of a given mass to charge ratio value the drift time for singly charged ions is slower than that of doubly charged ions. Although not shown in this plot, the corresponding drift time for triply charged ions is faster than that of doubly charged ions.

Figure 4:
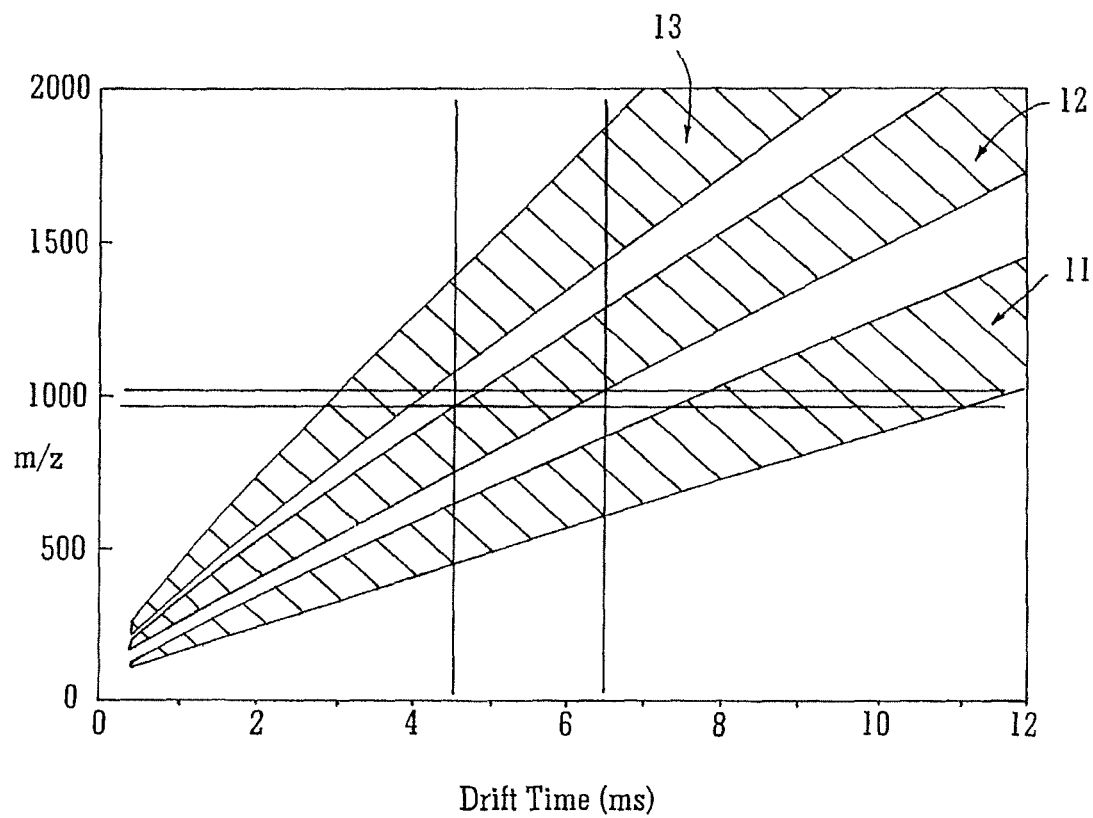
FIG. 4 shows bands of distribution of ion mobility drift time as a function of mass to charge ratio for singly, doubly and triply charged ions.

FIG. 4 shows bands containing the distribution of ion mobility drift times versus mass to charge ratio for singly charged ions 11, doubly charged ions 12 and triply charged ions 13. The bands for singly and doubly charged ions are in particular quite distinct.

FIG. 4 also illustrates the effect of limiting the transmission window. In this example, the first mass to charge ratio filter 2 can be considered as having been set to transmit ions having a mass to charge ratio of 1000. The mass to charge transmission window of the first mass to charge ratio filter has been shown to be quite wide in FIG. 4 for sake of illustration purposes only. In practice, the mass to charge ratio transmission window may be set to be 1 mass unit wide. The timing of the second ion gate 9 following the ion mobility spectrometer or separator 8 and upstream of the gas collision cell 10 was set to onwardly transmit only those ions which emerge from the ion mobility spectrometer or separator 8 between 4.5 ms and 6.5 ms from the start of the ion mobility experiment. Hence, in this example, only doubly charged ions having mass to charge ratios of 1000 would be onwardly transmitted by the second ion gate 9 to the gas collision cell 10. Any singly charged ions having a mass to charge ratio of 1000 which result, for example, from background chemical matrix would be excluded or prevented from reaching the gas collision cell 10 by the second ion gate 9.

FIG. 5A shows a mass spectrum obtained conventionally over the mass to charge ratio range 730 to 810 resulting from the consumption of 0.1 fmol of the tryptic digest of the protein β-lactoGlobulin. The mass spectrum shows the presence of peaks at every mass unit.

FIG. 5B shows a corresponding mass spectrum obtained over the same mass to charge ratio range for consumption of the same quantity of tryptic digest of the protein β-lactoGlobulin wherein singly charged ions resulting from the background chemical matrix were first removed according to a preferred embodiment of the present invention by using a mass to charge ratio filter in series or combination with an ion mobility filter and an ion gate. The mass spectrum shown in FIG. 5B shows that peaks at every mass unit have been removed and this reveals doubly charged peaks at half mass unit intervals and having a mass to charge ratio of 771. It is apparent that the detection limit and quantitation limit of the mass spectrometer has been significantly improved by at least an order of magnitude according to the preferred embodiment.

Figure 6A:
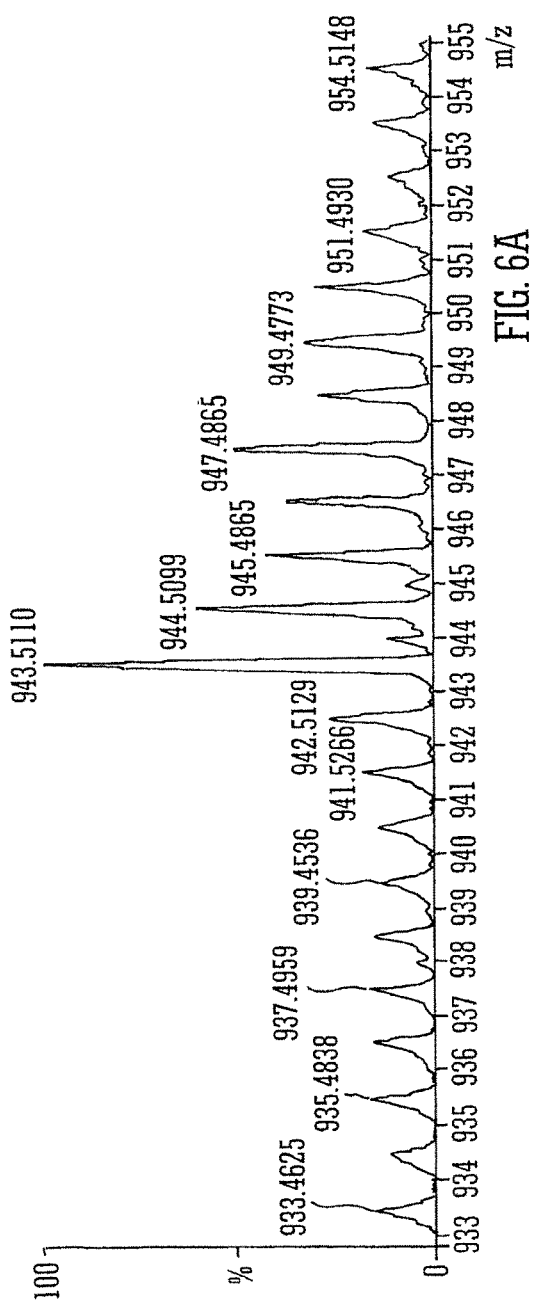
FIG. 6A shows a mass spectrum resulting from the tryptic digest of the protein Glycogen Phosphorylase B over the mass to charge ratio range 933 to 955 obtained conventionally and FIG. 6B shows a corresponding mass spectrum obtained by removing singly charged ions which result from background chemical matrix according to an embodiment of the present invention.

FIG. 6A shows a mass spectrum obtained in a conventional manner from the tryptic digest of the protein Glycogen Phosphorylase B over the mass to charge ratio range 933 to 955 using a MALDI ion source. The spectrum shows the presence of peaks at every mass unit.

Figure 6B:
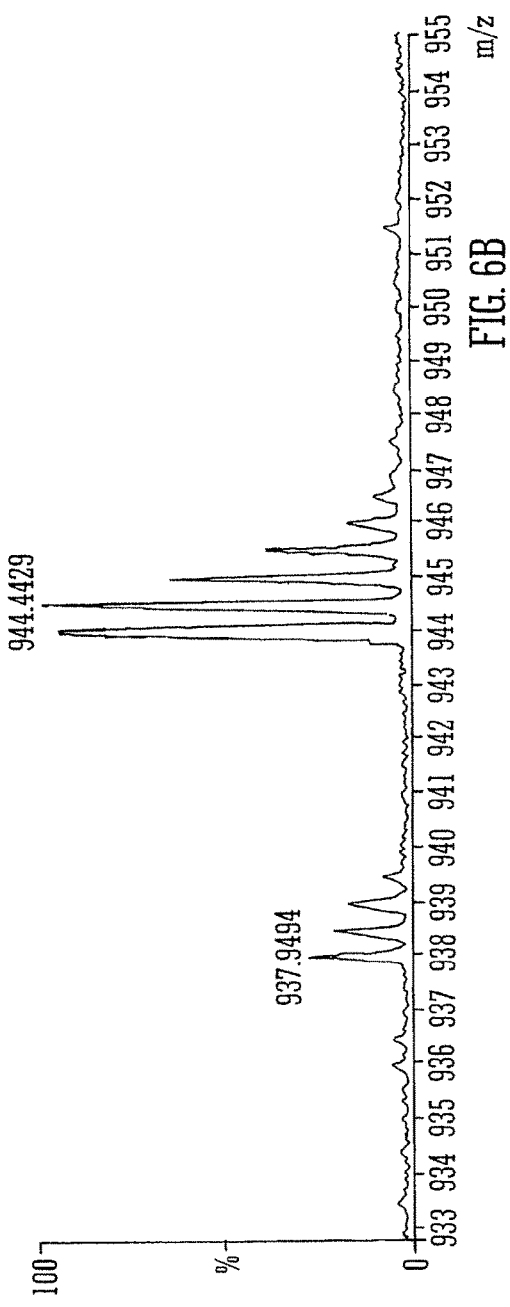

FIG. 6B shows a corresponding mass spectrum obtained from the tryptic digest of the protein Glycogen Phosphorylase B over the same mass to charge ratio range using a MALDI ion source but wherein singly charged ions resulting from the background chemical matrix were first removed according to a preferred embodiment of the present invention by using a mass to charge ratio filter in series or combination with an ion mobility filter and an ion guide. Again, the mass spectrum shows peaks at every mass unit have been removed and this reveals doubly charged peaks at half mass unit intervals having mass to charge ratios of 938 and 944. It is apparent that the detection limit and the quantitation limit of the mass spectrometer has been significantly improved by at least an order of magnitude according to the preferred embodiment.

Although the present invention has been described with reference to preferred embodiments, it will be understood by those skilled in the art that various changes in form and detail may be made without departing from the scope of the invention as set forth in the accompanying claims.

The invention claimed is:

1. A mass spectrometer comprising:
a first mass to charge ratio filter or mass to charge ratio mass analyser arranged and adapted in a first mode of operation to transmit ions having a mass to charge ratio within a first range;
an ion mobility spectrometer or separator adapted in a mode of operation to separate ions according to ion mobility such that ions having substantially the same mass to charge ratio within the first range will exit the ion mobility spectrometer or separator at substantially different times; and
attenuation means for attenuating ions in a mode of operation;
wherein said attenuation means is configured such that it is not mass-selective and such that it either substantially allows all ions to be onwardly transmitted, or substantially attenuates all ions by preventing all ions from being transmitted;
wherein said attenuation means comprises at least one of:
an ion gate or ion barrier arranged downstream of said ion mobility spectrometer or separator;
means for removing, attenuating or reducing the amplitude of an AC or RF voltage or potential which is applied to at least a portion of said ion mobility spectrometer or separator; and
means for removing, attenuating or reducing the amplitude of an AC or RF voltage or potential which is applied to at least a portion of an ion guide or other ion optical device arranged downstream of said ion mobility spectrometer or separator;
the mass spectrometer further comprising a control device configured to control the operation of said attenuation means;
wherein said control device is configured to control the operation of said attenuation means so that said attenuation means operates to transmit substantially all ions during a first time period or first time window, and said attenuation means operates to attenuate substantially all ions during a second time period or second time window, wherein said second time period or second time window is different from said first time period or first time window, wherein said second time period or second time window is selected such that operation of the attenuation means to attenuate substantially all ions during said second time period or second time window causes ions having mass to charge ratios within said first range but having one or more undesired first charge states to be attenuated.

2. A mass spectrometer as claimed in claim 1, further comprising a collision, fragmentation or reaction device.

3. A mass spectrometer as claimed in claim 1, wherein said first mass to charge ratio filter or mass to charge ratio mass analyser is arranged and adapted in said first mode of operation to attenuate ions having mass to charge ratios outside of said first range.

4. A mass spectrometer as claimed in claim 1, wherein said first undesired charge state is selected from one or more of the following: (i) singly charged; (ii) doubly charged; (iii) triply charged; (iv) quadruply charged; (v) quintuply; and (vi) multiply charged.

5. A mass spectrometer as claimed in claim 1, wherein said first mass to charge ratio filter or mass to charge ratio mass analyser is arranged upstream or downstream of said ion mobility spectrometer or separator.

6. A mass spectrometer as claimed in claim 1, further comprising an ion guide, ion trap or ion trapping region arranged upstream of said ion mobility spectrometer or separator, wherein said ion guide, ion trap or ion trapping region is arranged to trap, store or accumulate ions and then to periodically pulse ions into or towards said ion mobility spectrometer or separator.

7. A method of mass spectrometry using a mass spectrometer having an ion mobility spectrometer or separator, the method comprising:

transmitting ions having mass to charge ratios within a first range through a first mass to charge ratio filter or mass to charge ratio mass analyser;

separating ions according to ion mobility using the mobility spectrometer or separator, such that such that ions having substantially the same mass to charge ratio within the first range will exit the ion mobility spectrometer or separator at substantially different times; and attenuating ions in a mode of operation with attenuation means, wherein said attenuation means is configured such that it is not mass-selective and such that it either substantially allows all ions to be onwardly transmitted, or substantially attenuates all ions by preventing all ions from being transmitted, wherein said attenuation means comprises at least one of:

an ion gate or ion barrier arranged downstream of said ion mobility spectrometer or separator;

means for removing, attenuating or reducing the amplitude of an AC or RF voltage or potential which is applied to at least a portion of said ion mobility spectrometer or separator; and means for removing, attenuating or reducing the amplitude of an AC or RF voltage or potential which is applied to at least a portion of an ion guide or other ion optical device arranged downstream of said ion mobility spectrometer or separator wherein attenuating ions in a mode of operation with attenuation means comprises controlling the operation of said attenuation means so that said attenuation transmits substantially all ions during a first time period or first time window, and said attenuation means attenuates substantially all ions during a second time period or second time window, wherein said second time period or second time window is different from said first time period or first time window, wherein said second time period or second time window is selected such that operation of the attenuation means to attenuate substantially all ions during said second time period or second time window causes ions having mass to charge ratios within said first range but having one or more undesired first charge states to be attenuated.

8. A method as claimed in claim 7, wherein the mass spectrometer further comprises a collision, fragmentation or reaction device.

9. A mass spectrometer as claimed in claim 1, wherein said attenuation means comprises an ion gate or ion barrier arranged downstream of said ion mobility spectrometer or separator.

10. A mass spectrometer as claimed in claim 1, wherein said attenuation means comprises means for removing, attenuating or reducing the amplitude of an AC or RF voltage or potential which is applied to at least a portion of said ion mobility spectrometer or separator.

11. A mass spectrometer as claimed in claim 1, wherein said attenuation means comprises means for removing, attenuating or reducing the amplitude of an AC or RF voltage or potential which is applied to at least a portion of an ion guide or other ion optical device arranged downstream of said ion mobility spectrometer or separator.

12. A method as claimed in claim 7, wherein said attenuation means comprises an ion gate or ion barrier arranged downstream of said ion mobility spectrometer or separator.

13. A method as claimed in claim 7, wherein said attenuation means comprises means for removing, attenuating or reducing the amplitude of an AC or RF voltage or potential which is applied to at least a portion of said ion mobility spectrometer or separator.

14. A method as claimed in claim 7, wherein said attenuation means comprises means for removing, attenuating or reducing the amplitude of an AC or RF voltage or potential which is applied to at least a portion of an ion guide or other ion optical device arranged downstream of said ion mobility spectrometer or separator.

15. A mass spectrometer as claimed in claim 10, wherein when, in use, said attenuation means removes, attenuates or reduces the amplitude of an AC or RF voltage or potential which is applied to at least a portion of said ion mobility spectrometer or separator so that ions within at least a portion of said ion mobility spectrometer or separator are no longer confined radially within said ion mobility spectrometer or separator.

16. A mass spectrometer as claimed in claim 11, wherein when, in use, said attenuation means removes, attenuates or reduces the amplitude of an AC or RF voltage or potential which is applied to at least a portion of said ion guide or other ion optical device which is arranged downstream of said ion mobility spectrometer or separator then ions within at least a portion of said ion guide or other ion optical device are no longer confined radially within said ion guide or other ion optical device.

* * * * *